United States Patent
Bradbury et al.

(10) Patent No.: US 6,482,857 B1
(45) Date of Patent: Nov. 19, 2002

(54) COMPOSITIONS WHICH CONTAIN TRITERPENES FOR REGULATING HAIR GROWTH

(75) Inventors: Barton James Bradbury, West Chester; Shari Joy Soper; Joseph Robert Kaczvinsky, Jr., both of Cincinnati; Dorothy Limerick Bailey, Fairfield; Celeste Dawn Gale, Hamilton, all of OH (US)

(73) Assignee: The University of Texas Southwestern Medical Center, Dallas, TX (US)

( * ) Notice: Subject to any disclaimer, the term of this patent is extended or adjusted under 35 U.S.C. 154(b) by 0 days.

(21) Appl. No.: 09/353,409

(22) Filed: Jul. 15, 1999

Related U.S. Application Data

(60) Provisional application No. 60/093,192, filed on Jul. 17, 1998.

(51) Int. Cl.$^7$ .............................................. A61K 31/19
(52) U.S. Cl. ...................................... 514/557; 514/880
(58) Field of Search ......................................... 514/557

(56) References Cited

U.S. PATENT DOCUMENTS

| | | | | |
|---|---|---|---|---|
| 3,483,191 | A | 12/1969 | Krakower et al. | 260/239.7 |
| 3,483,225 | A | 12/1969 | Krakower et al. | 260/343.5 |
| 4,987,150 | A | 1/1991 | Kurono et al. | 514/455 |
| 5,480,913 | A | 1/1996 | Liao et al. | 514/732 |
| 5,523,090 | A | 6/1996 | Znaiden et al. | 424/401 |
| 5,529,769 | A | 6/1996 | Cho et al. | 424/74 |
| 5,536,499 | A | 7/1996 | Znaiden et al. | 424/401 |
| 5,567,419 | A | 10/1996 | Togiya et al. | 424/74 |
| 5,631,282 | A | 5/1997 | Goetz | 514/450 |
| 5,643,884 | A | 7/1997 | Anderson et al. | 514/26 |
| 5,674,497 | A | 10/1997 | Kuwana et al. | 424/195.1 |

FOREIGN PATENT DOCUMENTS

| | | | |
|---|---|---|---|
| DE | 19532006 | 3/1997 | A61K/31/19 |
| EP | 213809 | 3/1987 | A61K/35/78 |
| EP | 277455 | 8/1988 | A61K/7/06 |
| EP | 717983 | 6/1996 | A61K/7/48 |
| EP | 761661 | 3/1997 | |
| EP | 771795 | 5/1997 | |
| ES | 2017027 | 12/1990 | G01N/33/535 |
| FR | 2335234 | 7/1975 | A61K/35/78 |
| FR | 2705094 | 11/1994 | C07D/233/63 |
| FR | 2705097 | 11/1994 | C07D/257/04 |
| FR | 2723313 | 2/1996 | A61K/7/48 |
| FR | 2749510 | 12/1997 | A61K/7/42 |
| JP | 60126218 | 7/1985 | A61K/31/045 |
| JP | 6293215 | 4/1987 | A61K/7/06 |
| JP | 10017431 | 1/1988 | A61K/7/00 |
| JP | 01143832 | 6/1989 | A61K/31/32 |
| JP | 04290811 | 10/1992 | A61K/7/06 |
| JP | 05186326 | 7/1993 | A61K/7/48 |
| JP | 05276872 | 10/1993 | A23G/3/30 |
| JP | 05176688 | 11/1993 | A23K/1/16 |
| JP | 05286835 | 11/1993 | A61K/7/06 |
| JP | 06016525 | 1/1994 | A61K/7/06 |
| JP | 07010722 | 1/1995 | A61K/7/06 |
| JP | 08193094 | 7/1996 | |
| JP | 09067253 | 3/1997 | A61K/31/215 |
| JP | 09087156 | 3/1997 | A61K/7/48 |
| JP | 10265328 | 3/1997 | |
| JP | 09143050 | 6/1997 | A61K/7/48 |
| JP | 09151196 | 6/1997 | C07H/13/04 |
| JP | 09157139 | 6/1997 | A61K/7/06 |
| JP | 10025236 | 4/1998 | A61K/7/48 |
| RU | 2049462 | 12/1995 | A61K/7/035 |
| SU | 505621 | 3/1976 | C07C/35/22 |
| SU | 1214679 | 2/1986 | C08C/63/52 |
| SU | 1325881 | 8/1991 | C07J/53/00 |
| SU | 1401872 | 8/1991 | C07J/53/00 |
| SU | 1671666 | 8/1991 | C07J/63/00 |
| WO | 9014764 | 12/1990 | A61K/31/045 |
| WO | 9216186 | 10/1992 | A61K/7/06 |
| WO | 9209262 | 10/1993 | A61K/7/48 |
| WO | 9535103 | 12/1995 | A61K/31/045 |
| WO | 9629068 | 9/1996 | A61K/31/19 |
| WO | 9638173 | 12/1996 | A61K/45/00 |
| WO | 9701346 | 1/1997 | A61K/35/78 |
| WO | 9705887 | 2/1997 | A61K/35/78 |
| WO | 9716182 | 5/1997 | A61K/31/335 |

OTHER PUBLICATIONS

Inada et al, Chem. Pharm. Bull, 41(3) 617–619, 1993.*
JICST–EPLUS AN 930341339, Inada et al, 'Phytochemical studies on meliaceous plants. VII, Structures and inhibitory effects on Epstein–Barr Virus Activation of triterpenoids from leaves of *Chisocheton mactophyllus* king', Chem. Pharm, Bull, 41(3), 617–619, 1993.*
Mizuno et al., "Cosmetics containing POV elevation inhibitors and lipase inhibitors" abstract, JP09118611, May 1997.
Hayashi et al., "Hair growth stimulants containing .alpha.–amyrin . . . ", abstract, JP07010722, Jan. 1995.
Okazaki et al., "Hair tonics containing oleanolic acid derivatives" abstract JP62093215, Apr. 1987.
Wang et al., "Qualitative analysis of Chinese drug Xiakicao (Prunella)." Abstract, Zhongguo Zhongyao Zazhi, 1993, vol. 18(11), pp. 655–7.
Tsuji et al., "Hair growth stimulants containing triterpenes" abstract JP09157139, Jun. 1997.

* cited by examiner

*Primary Examiner*—Rebecca Cook
(74) *Attorney, Agent, or Firm*—Michael Best & Friedrich LLP

(57) ABSTRACT

The present invention relates to compositions containg i) from about 0.0001% to about 99.9% of certain compounds selected from the group consisting of lupane triterpenes, derivatives of lupane triterpenes, derivatives of oleanane triterpenes, derivatives of ursane triterpenes, and salts and mixtures thereof, and ii) a vehicle.

4 Claims, No Drawings

COMPOSITIONS WHICH CONTAIN TRITERPENES FOR REGULATING HAIR GROWTH

CROSS-REFERENCE TO RELATED APPLICATIONS

This patent application claims priority, under 35 U.S.C. § 119, to provisional patent application No. 60/093,192 filed on Jul. 1, 1998.

TECHNICAL FIELD

The present invention relates to compositions which contain certain compound selected from the group consisting of lupane triterpenes; derivatives of lupane triterpenes; derivatives of oleanane triterpenes; derivatives of ursane triterpenes; and salts and mixtures thereof. These compositions are useful for regulating hair growth.

BACKGROUND

Society in general continues to attach a stigma to hair loss. As a result, men and women who suffer from hair loss often experience self-consciousness relating to the condition. Many methods of "curing" hair loss have been disclosed in the literature and several products claiming to regulate hair growth are currently marketed.

One approach for growing hair involves the much publicized use of minoxidil (Rogaine®)(6-(1-piperidinyl)-2,4-pyrimidinediamine 3-oxide), a potent antihypertensive agent, as a hair growth promoting agent (see U.S. Pat. Nos. 3,461,461; 3,973,061; 3,464,987; and 4,139,619). Unfortunately, not all people respond to minoxidil and the efficacy level is limited in those individuals who do exhibit a response.

Finasteride (Propecia®) is another currently marketed product for promoting hair growth. See EP 823436; U.S. Pat. No. 5,670,643; WO 97/15564; and WO 97/15558. Unfortunately, as with minoxidil, not all people respond to fmesteride and the efficacy is limited in those people who do exhibit a response. Moreover, the use of finesteride has been associated with reduced libido, teratagenic effects and other side effects in certain individuals.

Another approach for "curing" hair loss involves a procedure of weaving synthetic or natural hair strands into the remaining hair strands of the subject. Such a procedure is time-consuming, expensive and requires follow-up re-weavings as the weaves loosen and/or the subject's existing hair strands grow. Furthermore, such a procedure does not cure hair loss, but merely masks the condition.

Another approach for treating hair loss is the use of hair plugs. This procedure involves the transplantation of terminal hair follicles from regions of normal hair growth on the subject's scalp to regions of thinning or no hair growth on the scalp. This procedure is time consuming, expensive and can be painful. Furthermore, the transplanted plugs, at least in the early stages following transplantation, produce an unnatural look to the scalp.

Thus, there is a need for an easily administered, efficacious agent for treating hair loss in a mammal, which agent has little or no undesirable side effects.

SUMMARY OF THE INVENTION

The present invention relates to compositions containing:
i) from about 0.00001% to about 99.9% of a compound selected from the group consisting of:

a) lupane triterpenes having the structure:

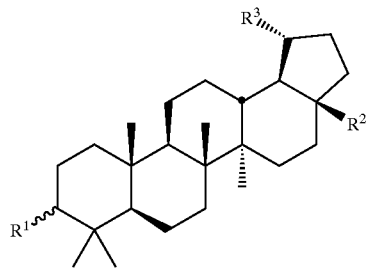

Where $R^1$ is either
1) connected to the ring system via a single bond, either α- or β- configuration, and is selected from the group consisting of: H, OH, $R^4$, $OR^4$, $OCOR^4$, $OCOOR^4$, $OCONHR^4$, $OCON(R^4)_2$: or halogen where $R^4$ is independently selected from the group consisting of a) cyclic, straight chain or branched chain, saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$, vi) $OCOOR^4$, vii) $OCONHR^4$, or viii) $OCON(R^4)_2$ and b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$), or
2) connected to the ring system via a double bond and is selected from the group consisting of a) oxygen, b) sulfur and c) $R^4$, Where $R^2$ is selected from the group consisting of: $CH_3$, $CH_2OH$, $CH_2OR^4$, CHO, $CO_2H$, $CO_2R^4$, $COHNR^4$, $CON(R^4)_2$, $CH^2OCOR^4$ where $R^4$ is independently selected from the group consisting of a) cyclic, straight chain or branched chain, saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$ vi) $OCOOR^4$, vii) $OCONHR^4$, or viii) $OCON(R^4)_2$; and b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$;

And where $R^3$ is selected from the group consisting of $C(CH_3)=CH_2$, $CH(CH_3)_2$, $COCH_3$, $CH(OH)CH_3$, $CH_2CH_3$, $C(R^5)(CH_3)CH_2R^5$, or $C(CH_3)_2R^5$, $CH(CH_3)CH_2$ the group consisting of OH and a halogen, b) compounds having the structure:

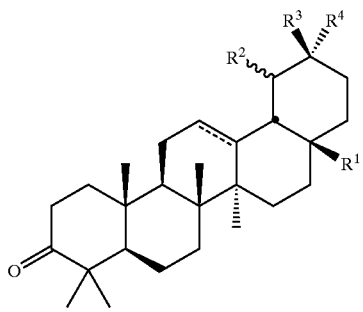

where $R_1$ is selected from the following groups: $CH_3$, $CH_2OH$, $CH_2OR^4$, CHO, $CO_2H$, $CO_2R^4$, $COHNR^4$, $CON(R^4)_2$, $CH^2OCOR^4$ where $R^4$ is independently selected from the group consisting of 1) cyclic, straight chain or branched chain , saturated or unsaturated, substituted or unsubstituted alkyl groups containing from 1–20 carbons, where the alkyl group, if substituted, is substituted with a substituent selected from the group consisting of: a) halogens, b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ c) OH, d), $OR^4$, e) $OCOR^4$, f) $OCOOR^4$, g) $OCONHR^4$, or h) $OCON(R^4)_2$ and 2) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$);

where $R_2=CH_3$ or H,
where $R_3=CH_3$ or H, and
where $R_4=CH_3$ or H; and c) compounds having the structure:

i)
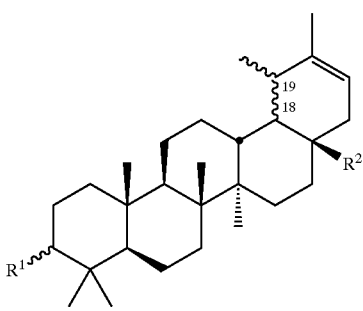

ii)
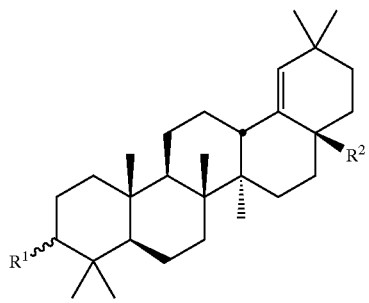

Where $R^1$ is either
1) connected to the ring system via a single bond, either α- or β-configuration, and is selected from the group consisting of: H, OH, $R^4$, $OR^4$, $OCOR^4$, $OCOOR^4$, $OCONHR^4$, or $OCON(R^4)_2$: halogen where $R^4$ is independently selected from the group consisting of a) cyclic, straight chain or branched chain, saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$, vi) $OCOOR^4$, vii) $OCONHR^4$, or viii) $OCON(R^4)_2$ and b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$), or
2) connected to the ring system via a double bond and is selected from the group consisting of a) oxygen, b) sulfur and c) $R^4$, and Where $R^2$ is selected from the group consisting of: $CH_3$, $CH_2OH$, $CH_2OR^4$, CHO, $CO_2H$, $CO_2R^4$, $COHNR^4$, $CON(R^4)_2$, $CH^2OCOR^4$ where $R^4$ is independently selected from the group consisting of a) cyclic, straight chain or branched chain , saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$ vi) $OCOOR^4$, vii) $OCONHR^4$, or viii) $OCON(R^4)_2$ d) salts of the acid forms of (a), (b) or (c);
e) mixtures of (a), (b), (c) Or (d),
wherein the compound is not comprised solely of betulinic acid; and ii) a vehicle.

DETAILED DESCRIPTION OF THE INVENTION

The present invention relates to compositions containing certain compounds selected from the group consisting of lupane triterpenes, derivatives of lupane triterpenes, derivatives of oleanane triterpenes, derivatives of ursane triterpenes, derivatives of taraxastane triterpenes, and salts and mixtures thereof. Such compositions are useful for regulating hair growth. As used herein, the term "regulating hair growth" means increasing the rate of hair growth and/or inducing the formation of a greater number of hair strands, and/or increasing the diameter of the hair strand, and/or lengthening the hair strand, and/or changing the hair follicle from vellus to terminal, and/or converting follicles from telogen to anagen phase (thereby increasing the overall ratio of anagen phase follicles relative to telogen phase follicles) and/or preventing, retarding, or arresting the process of hair loss, and/or treating alopecias.

As used herein, "vellus hair follicle" means a hair follicle which produces a soft, short, and often colorless hair fiber. The size of the vellus follicle is considerably smaller than the terminal hair follicle. In an adult, vellus follicles can be found on the forehead (i.e, receding hair line area) and bald scalp.

As used herein, "terminal follicle" means a hair follicle which produces a coarse, long and often pigmented hair shaft. The size of the terminal follicle is considerably larger, thicker in diameter and longer than the vellus follicle. In an adult, terminal follicles can be found on the scalp, axilla and pubic areas.

As used herein, "anagen phase" refers to the period in the hair follicle growth cycle wherein the follicle is actively growing and producing new hair.

As used herein, "telogen phase" refers to the period in the hair growth cycle wherein the follicle is resting and not producing new hair.

The compositions of the present invention, as well as method for manufacture and method using, are described in detail as follows:

I. THE COMPOSITIONS

The compositions of the present invention contain i) certain compounds selected from the group consisting of lupane triterpenes, derivatives of acid triterpenes, derivatives of oleanane triterpenes, derivatives of ursane triterpenes, derivatives of taraxastane triterpenes, and salts and mixtures thereof, and ii) a vehicle.

The compositions of the present invention can be administered topically, orally or parenterally. In a preferred embodiment of the present invention, the compositions of the present invention are administered topically. Topical compositions of the present invention can be in any form, including but not limited to creams, gels, lotions, shampoos, rinses, tonics, sprays, ointments, mousses, or pomades.

The ingredients comprising the compositions herein, as well as other optional components, are described in detail as follows:

A. Lupane Triterpenes, Derivatives of Lupane Triterpenes, Derivatives of Oleanane Triterpenes, Derivatives of Ursane Triterpenes and Salts and Mixtures Thereof The compositions of the present invention contain from about 0.00001% to about 99.9%, preferably from about 0.001 to about 75%, more preferably from about 0.001% to about 50%, even more preferably from about 0.01% to about 25% and most preferably from about 0.1% to about 15% of a compound selected from the group of lupane triterpene acids, certain derivatives of lupane triterpenes, certain derivatives of oleanane triterpenes, certain derivatives of ursane triterpenes, certain derivatives of taraxastane triterpenes and salts and mixtures thereof.

Lupane triterpenes have the general structure:

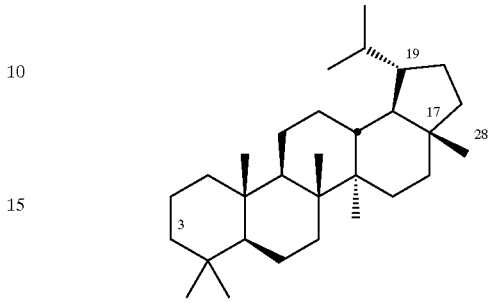

The term "derivatives of lupane triterpenes" as used herein includes compounds which have additional substituents on this skeleton, double bonds in place of single bonds, changes in stereochemistry or relocated methyls and/or isopropyl groups.

Preferred lupane triterpenes and lupane triterpene derivatives of the present invention are those represented by the structure:

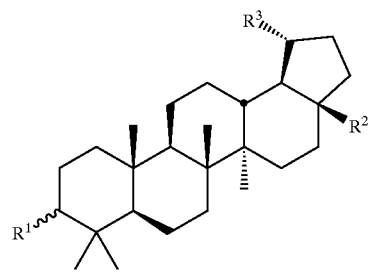

Where $R^1$ is either
1) connected to the ring system via a single bond, either α- or β-configuration, and is selected from the group consisting of: H, OH, $R^4$, $OR^4$, $OCOR^4$, $OCOOR^4$, $OCONHR^4$, or $OCON(R^4)_2$: halogen where $R^4$ is independently selected from the group consisting of a) cyclic, straight chain or branched chain, saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$, vi) $OCOOR^4$, vii) $OCONHR^4$, or viii) $OCON(R^4)_2$ and b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$), or 2) connected to the ring system via a double bond and is selected from the group consisting of a) oxygen, b) sulfur and c) $R^4$, Where $R^2$ is selected from the group consisting of: $CH_3$, $CH_2OH$, $CH_2OR^4$, $CHO$, $CO_2H$, $CO_2R^4$, $COHNR^4$, $CON(R^4)_2$, $CH^2OCOR^4$ where $R^4$ is independently selected from the group consisting of a) cyclic, straight chain or branched chain, saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$ vi) $OCOOR^4$, vii) $OCONHR^4$, or viii) $OCON(R^4)_2$; and b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$;

And where $R^3$ is selected from the group consisting of $C(CH_3)=CH_2$, $CH(CH_3)_2$, $COCH_3$, $CH(OH)CH_3$, $CH_2CH_3$, $C(R^5)(CH_3)CH_2R^5$, or $C(CH_3)_2R^5$, $CH(CH_3)CH_2$ the group consisting of OH and a halogen, Preferably, if $R^4$ comprises an alkyl group, the alkyl group is unsubstituted.

Preferably $R^1$ is selected from the group consisting of H, OH, $OCOOR^4$ and $OCON(R^4)_2$ Preferably $R^2$ is selected from the group consisting of $CH_3$, $CH_2OH$, $CH_2OR^4$, $CHO$, $COHNR^4$, and $CON(R^4)$.

Especially preferred lupane triterpenes for use herein include betulinic acid, betulonic acid, betulin and derivatives and salts and mixtures thereof. Betulinic acid, betulonic acid and mixtures thereof are most preferred for use herein.

Betulinic acid has the following structure:

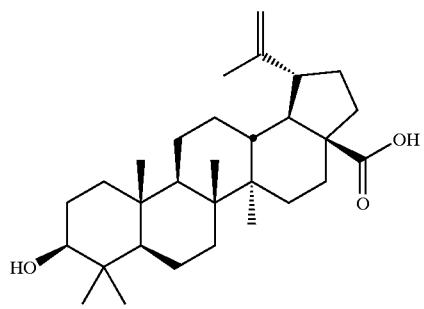

Betulinic acid may be obtained commercially as pure betulinic acid, synthesized according to known methods, or can be extracted from a plant. Non-limiting examples of genuses of plants which may contain betulinic acid are as follows:

| | | | |
|---|---|---|---|
| Acacia | Acanthopanax | Aconitum | Acrotrema |
| Actinobale | Adansonia | Adina | Agrostistachys |
| Ailanthus | Akania | Alangium | Alchemilla |
| Aleurites | Alnus | Alphitexolide | Amanoa |
| Ammannia | Amorphophallus | Ampelozizyphus | Amsonia |
| Anaxeton | Anemone | Anticharis | Arbutus |
| Arctostaphylos | Artocarpus | Aspidixia | Avicennia |
| Bauhinia | Bencomia | Betula | Bischofia |
| Boehmeria | Bonnetia | Bowdichia | Bretschneidera |
| Broussonctia | Buxus | Byrsonima | Caesalpinia |
| Calicarpa | Callicarpa | Callistemon | Calophyllum |
| Camptotheca | Canthium | Caraipa | Casearia |
| Cassia | Cassinia | Ceanothus | Celosia |
| Cerberiopsis | Chamaecrista | Chisocheton | Clerodendron |
| Clinopodium | Clusia | Coccoloba | Coleus |
| Colubrina | Corchoros | Comus | Cotoneaster |
| Cottonrose | Crataeva | Crossopteryx | Crotalaria |
| Curatela | Cylicodiscus | Dendriopoterium | Dendrocatamus |
| Derris | Dichrostachys | Dicoma | Digera |
| Dillenia | Diospyros | Dipterocarpus | Discaria |
| Doliocarpus | Dryobalanops | Duboisia | Echinops |
| Ehretia | Emmenospennum | Engelhardtia | Enkianthus |
| Enterolobium | Epigaea | Epilobium | Epithelantha |
| Eryngium | Erythmspermum | Eucalyptus | Euclea |
| Eucommia | Eugenia | Euphorbia | Euptelea |
| Eurya | Fagonia | Fagus | Ficus |
| Formosia | Forsythia | Fraxinus | Gardenia |
| Gaultheria | Givotia | Glycyrrhiza | Gochnatia |
| Gypsophila | Hedyotis | Helicteres | Heliotropium |
| Hippophae | Hoffmannia | Holoptelea | Hydnocarpus |
| Hypericum | Ilyptis | Inga | Iris |
| Jacaranda | Jasminum | Juglans | Kayea |
| Koompassia | Lantana | Lavandula | Lawsonia |
| Lepechinia | Leptospennum | Lespedeza | Leucothoe |
| Liana | Licania | Limnophila | Linaria |
| Liquidambar | Lithocarpus | Lusia | Lychnophora |
| Lycopus | Lythrum | Madhuca | Maytenus |
| Melaleuca | Melanoxylon | Melastoma | Melilotus |
| Menyanthes | Mesua | Micromeria | Mimusops |
| Mitrephora | Monttea | Morus | Myodocarpus |
| Nelumbo | Nerium | Nymphoides | Nyssa |
| Olea | Oplopanax | Origanum | Paeonia |
| Pavonia | Pedilanthus | Phellinus | Phyllanthus |
| Phyllodoce | Physochlaina | Picramnia | Pieris |
| Platyphylla | Plumeria | Poiygonum | Pongamia |
| Pouteria | Prunella | Psychotria | Putoria |
| Pygeum | Pyracantha | Pyrus | Quercus |
| Relbania | Rhododendron | Rosa | Rosmarinus |
| Roylea | Salvia | Sapium | Sarracenia |
| Schefflera | Schleichera | Schrebera | Scirpus |
| Sclerolobium | Scolapia | Scoparia | Senecio |
| Senna | Shorea | Solanum | Sorocea |
| Sphagnum | Spiraea | Spondianthus | Symplocus |
| Syzigium | Tabebuia | Tacca | Talguenea |
| Tectona | Tephrosia | Terminalia | Tetracera |
| Tinospora | Tovoniita | Transcaucasian | Triadenum |
| Tripetaleia | Tripetalia | Triphyophyllum | Tu-Jin-Pi |
| Vauquelinia | Vellozia | Viscum | Vismia |
| Visnea | Vitis | Vochysia | Wisteria |
| Woodfordia | Wormia | Zizyphus | |

Betulonic acid has the following structure:

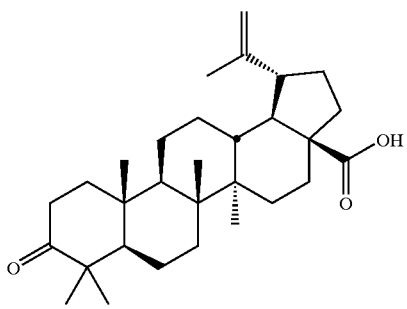

Betulonic acid may be obtained commercially as pure betulonic acid, can be synthesized according to known methods or can be extracted from a plant which contains betulonic acid.

The following are nonlimited examples of genuses of plants which may contain betulonic acid:

| | | | |
|---|---|---|---|
| Acanthopanax | Akania | Alphitonia | Anisomcles |
| Betula | Boronia | Bursera | Cacosmia |
| Chisocheton | Dillenia | Dipterocarpus | Duboisia |
| Elaeodendron | Eucalyptus | Euonymus | Euphorbiaceae |
| Flacourtiaceae | Glochidion | Helichrysum | Lantana |
| Liquidambar | Maytenus | Orthopterygium | Quercus |
| Rhododendron | Rhodomyntus | Roylea | Symphyopappus |
| Velozia | Vibumum | Zizyphus | |

Betulin has the following structure:

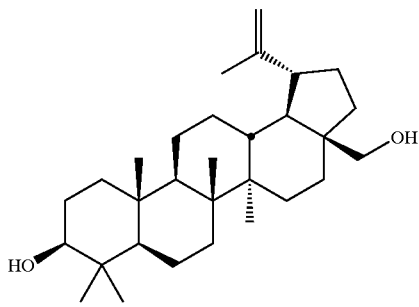

Betulin can be obtained commercially as pure betulin, can be synthesized according to known methods or can be extracted from plants which contain betulin. Non-limiting examples of genuses plants which may contain betulin are those previously listed for betulinic acid.

The plant extracts containing lupane triterpenes are extracted by organic solvent extracts, e.g., hexane extracts, chloroform extracts, alcoholic extracts, ethyl acetate extracts, propylene glycol extracts, ethylene glycol extracts, and ether extracts Extraction procedures for extracting the plant extracts are well known to persons skilled in the art. Extraction can be carried out on a crushed material, which is introduced into the extraction solvent. The extraction can be repeated several times until the material is used up, in accordance with procedures which are well known to persons skilled in the art. The extraction can be carried out at room temperature, or with heating, notably with reflux of the solvent. The proportion by weight between the solvent and the material to be extracted can vary within broad limits and can be, for example, between 1:1 and 10:1.

Certain derivatives of oleanane triterpenes and ursane triterpenes can also be desirably incorporated into the compositions of the present invention. Such derivatives have the structure:

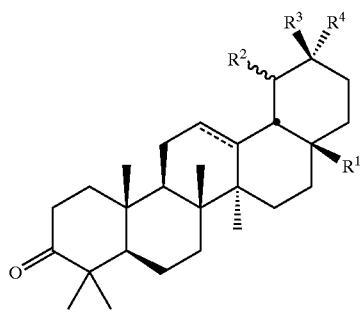

where $R_1$ is selected from the following groups: $CH_3$, $CH_2OH$, $CH_2OR^4$, $CHO$, $CO_2H$, $CO_2R^4$, $COHNR^4$, $CON(R^4)_2$, $CH_2OCOR^4$ where $R^4$ is independently selected from the group consisting of a) cyclic, straight chain or branched chain, saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$ vi) $OCOOR^4$, vii) $OCONHR^4$, or viii) $OCON(R^4)_2$ and b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$), where $R_2=CH_3$ or H, where $R_3=CH_3$ or H, and where $R_4=CH_3$ or H.

Preferred derivatives of oleanane triterpenes and ursanes triterpenes are ursonic acid (3-oxo-urs-12-en-28-oic acid) and oleanonic acid (3-oxo-olean-12-en-28-oic acid) and mixtures thereof.

Ursonic acid has the structure:

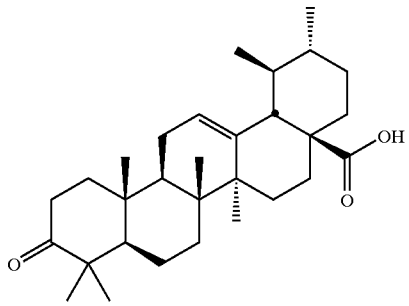

Ursonic acid can be obtained commercially as 100% ursonic acid, can be synthesized according to known methods or can be extracted from plants which contain ursonic acid.

Oleanonic acid has the structure:

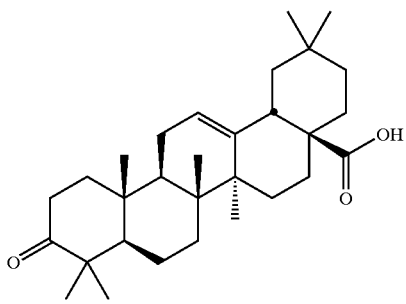

Oleanonic acid can be obtained commercially as 100% oleanonic acid, can be synthesized according to known methods or can be extracted from plants which contain oleanoinic acid.

Derivatives of taraxastane triterpenes can also be desirably incorporated into the compostions of the present invention. Derivatives of taraxastane triterpenes suitable for use herein have the structure:

a)
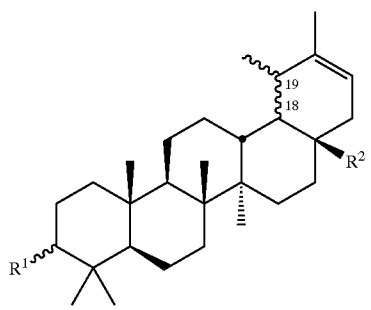

b)
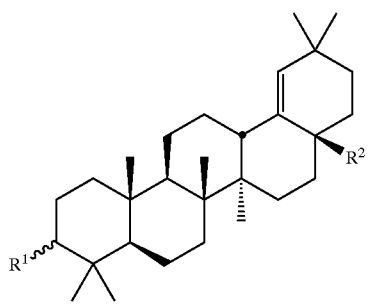

Where $R^1$ is either
1) connected to the ring system via a single bond, either α- or β-configuration, and is selected from the group consisting of: H, OH, $OR^4$, $R^4$, $OCOR^4$, $OCOOR^4$, $OCONHR^4$, or $OCON(R^4)_2$: halogen where $R^4$ is independently selected from the group consisting of a) cyclic, straight chain or branched chain, saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$, iii) OH, iv), $OR^4$, v) $OCOR^4$, vi) $OCOOR^4$, vii) $OCONHR^4$, or viii) $OCON(R^4)_2$ and b) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$), or 2) connected to the ring system via a double bond and is selected from the group consisting of a) oxygen, b) sulfur and c), and Where $R^2$ is selected from the group consisting of: $CH_3$, $CH_2OH$, $CH_2OR^4$, CHO, $CO_2H$, $CO_2R^4$, $COHNR^4$, $CON(R^4)_2$, $CH^2OCOR^4$ where $R^4$ is independently selected from the group consisting of a) cyclic, straight chain or branched chain , saturated or unsaturated, substituted or unsubstituted alkyl groups containing from 1–20 carbons, where the alkyl group, if substituted, is substituted with a substituent selected from the group consisting of: i) halogens, ii) substituted or unsubstituted aryl groups comprising from 1 to 5 rings with or without heteroatoms, which heteroatoms are selected from the group consisting of nitrogen, oxygen or sulfur, where the aryl group, if substituted, is substituted with a substituent selected from the group consisting of halogens, alkyl groups, OH, $OR^4$, $OCOR^4$, $OCOOR^4$, $OCONHR^4$, or $OCON(R^4)_2$ iii) OH, iv), $OR^4$, v) $OCOR^4$, vi) $OCOOR^4$, vii) $OCONHR^4$, or viii) $OCON(R^4)_2$ Suitable salts of the triterpene acids described herein which are suitable for use herein include ammonium, organic amines (e.g., alkylamines, wherein the alkyl group is linear, branched or cyclic), and metal salts. Specific non-limiting examples of suitable salts for use herein include ammonium, isopropyl amine, morpholine, piperdine, sodium, potassium, calcium, magnesium, zinc, aluminum, and copper salts.

B. Vehicle

The compositions which are utilized in the method of the present invention preferably also contain a solid, semi-solid or liquid cosmetically or pharmaceutically acceptable vehicle to act as a diluent, dispersant or carrier for the active components in the composition. As used herein, "pharmaceutically-acceptable" means that drugs, medications or inert ingredients which the term describes are suitable for use in humans and lower animals without undue toxicity, incompatibility, instability, irritation, allergic response, and the like. As used herein, "cosmetically acceptable" means that ingredients which the term describes are suitable for use in contact with the skin or hair of humans and lower animals without undue toxicity, incompatibility, instability, irritation, allergic response and the like. The cosmetically or pharmaceutically acceptable vehicles comprise from about 0.1% to about 99.999%, preferably from about 25% to about 99.99%, more preferably from about 50% to about 99.99%, even more preferably from about 75% to about 99.9%, most preferably from about 85% to about 99.9% by weight of the composition.

Acceptable vehicles include, for example, water, lipophilic or hydrophilic emollients/humectants, surfactants, thickeners, powders, polymers, resins, plasticizers, fillers, lubricants, binders, disintegrants, solvents, co-solvents, buffer systems, preservatives, sweetening agents, flavoring agents, pharmaceutical grade dyes and pigments 1. Water Water can be employed in the compositions herein as a vehicle. When water is employed as the vehicle, the composition will be in the form of an emulsion, suspension or cream.

2. Lipophilic or Hydrophilic Emollients/Humectants

Hydrophilic or lipophilic emollients and/or humectants can be incorporated into the compositions herein as the vehicle at levels ranging from about 0.5% to about 85%, preferably from about 5% to about 50%, more preferably from about 10% to about 30% by weight of the composition. Suitable emollients and humectants are listed in *CTFA Cosmetic Ingredient Handbook*, Second Edition, 1992, pp. 572–575, which is herein incorporated by reference. Suitable emollients/humectants include esters, fatty acids and alcohols, polyols, hydrocarbons, silicones, waxes, triglycerides, cationic and nonionic polymers and mixtures thereof.

a. Esters

C1–C30 alcohol esters of C1–C30 carboxylic acids and of C2–C30 dicarboxylic acids, including straight and branched chain materials as well as aromatic derivatives can also be used herein. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Non-limiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

b. Fatty Alcohols and Fatty Acids

Suitable fatty alcohols and acids include those compounds having from 10 to 20 carbon atoms. Especially preferred are such compounds as cetyl, myristyl, palmitic and stearyl alcohols and acids.

c. Polyols

Among the polyols which are useful as a vehicle herein are linear and branched chain alkyl polyhdyroxyl compounds. Preferred polyols include propylene glycol, sugars having up to about 12 carbons atoms, sugar alcohols having up to about 12 carbon atoms, and mixtures thereof, glycerin, polypropylene glycols, polyethylene glycols, ethyl hexane diol, hexylene glycols, ureas and mixtures thereof.

Specific examples of useful polyols include materials such as urea; guanidine; glycolic acid and glycolate salts (e.g. ammonium and quaternary alkyl ammonium); lactic acid and lactate salts (e.g. ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; and mixtures thereof. Also useful are materials such as aloe vera in any of its variety of forms (e.g., aloe vera gel), chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990, which is incorporated by reference herein in its entirety.

d. Hydrocarbons

Suitable hydrocarbons are straight and branched chain hydrocarbons having anywhere from 7 to 40 carbon atoms. Non-limiting examples include mineral oil, petrolatum, squalene, isoparaffins. dodecane, isododecane, cholesterol, hydrogenated polyisobutylene, docosane (i.e. a $C_{22}$ hydrocarbon), hexadecane, isohexadecane (a commercially available hydrocarbon sold as Permethyl ® 101A by Presperse, South Plainfield, N.J.).

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

e. Silicones

Nonvolatile silicones such as polydialkylsiloxanes, polydiarylsiloxanes, and polyalkarylsiloxanes are also useful herein. These silicones are disclosed in U.S. Pat. No. 5,069,897, to Orr, issued Dec. 3, 1991, which is incorporated by reference herein in its entirety. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, non-limiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_3)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

f. Waxes

Waxes which are potentially useful as the vehicle in the compositions herein include those set forth in *CTFA Cosmetic Ingredient Handbook*, Second Edition, 1992, pp. 535, which is herein incorporated by reference. Specific examples include beeswax, carnauba, candelilla wax, jojoba wax, lanolin wax, ozokerite, paraffin wax, and mixtures thereof g. Triglycerides Animal fats, vegetable oils and hydrogenated vegetable oils, and vegetable oil adducts are also potentially useful herein.

Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

3. Surfactants

Surfactants can be desirably utilized as the vehicle in the compositions herein. Surfactants, if used, are typically employed at levels ranging from about 0.1% to about 30%, preferably from about 0.1% to about 10%, more preferably from about 0.1% to about 5% by weight of the composition. Suitable surfactants for use herein include cationic, nonionic, anionic, amphoteric and combinations thereof.

Non-limiting examples of anionic surfactants useful in the compositions of the present invention are disclosed in McCutcheon's, *Detergents and Emulsifiers*, North American edition (1986), published by allured Publishing Corporation; McCutcheon's, *Functional Materials*, North American Edition (1992); and U.S. Pat. No. 3,929,678, to Laughlin et al., issued Dec. 30, 1975 all of which are incorporated by reference herein in their entirety.

A wide variety of anionic surfactants are useful herein. Non-limiting examples of anionic surfactants include those selected from the group consisting of sarcosinates, sulfates, isethionates, taurates, phosphates, and mixtures thereof. Amongst the isethionates, the alkoyl isethionates are preferred, and amongst the sulfates, the alkyl and alkyl ether sulfates are preferred. The alkoyl isethionates typically have the formula $RCO-OCH_2CH_2SO_3M$ wherein R is alkyl or alkenyl of from about 10 to about 30 carbon atoms, and M is a water-soluble cation such as ammonium, sodium, potassium and triethanolamine. Non-limiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials include the sarcosinates, non-limiting examples of which include sodium lauroyl sarcosinate, sodium cocoyl sarcosinate, and ammonium lauroyl sarcosinate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety.

Non-limiting examples of preferred anionic surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl sarcosinate, and mixtures thereof.

Non-limiting examples of nonionic surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g. C8–30 alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$- moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

The term "amphoteric surfactant," as used herein, is also intended to encompass zwitterionic surfactants, which are well known to formulators skilled in the art as a subset of amphoteric surfactants.

A wide variety of amphoteric surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH$_2$)$_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

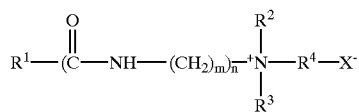

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are CH$_3$; X is selected from the group consisting of CO$_2$, SO$_3$ and SO$_4$; $R^4$ is selected from the group consisting of saturated or unsaturated, straight or branched chain alkyl, unsubstituted or monosubstituted with hydroxy, having from 1 to about 5 carbon atoms. When X is CO$_2$, $R^4$ preferably has 1 or 3 carbon atoms, more preferably 1 carbon atom. When X is SO$_3$ or SO$_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

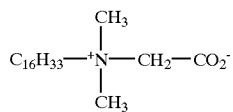

Cocamidopropylbetaine

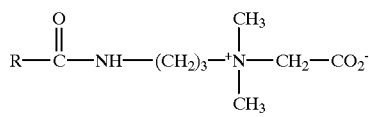

wherein R has from about 9 to about 13 carbon atoms

Cocamidopropyl hydroxy sultaine

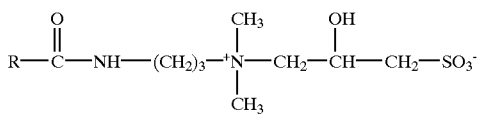

wherein R has from about 9 to about 13 carbon atoms,

Examples of other useful amphoteric surfactants are alkyliminoacetates, and iminodialkanoates and aminoalkanoates of the formulas RN[(CH$_2$)$_m$CO$_2$M]$_2$ and RNH(CH$_2$)$_m$CO$_2$M wherein m is from 1 to 4, R is a C$_8$–C$_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Non-limiting examples of cationic surfactants useful herein are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Non-limiting examples of cationic surfactants useful herein include cationic alkyl ammonium salts such as those having the formula:

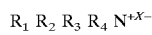

wherein $R_1$, is selected from an alkyl group having from about 12 to about 18 carbon atoms, or aromatic, aryl or alkaryl groups having from about 12 to about 18 carbon atoms; $R_2$, $R_3$, and $R_4$ are independently selected from hydrogen, an alkyl group having from about 1 to about 18 carbon atoms, or aromatic, aryl or alkaryl groups having from about 12 to about 18 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 18 carbon atoms; $R_2$ is selected from H or an alkyl group having from about 1 to about 18 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 18 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5$CO-(CH$_2$)$_n$-, wherein $R_5$ is an alkyl group having from about 12 to about 22 carbon atoms, and n is an integer from about 2 to about 6, more preferably from about 2 to about 4, and most preferably from about 2 to about 3. Non-limiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Non-limiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

4. Thickeners/Binders

Another category of functional ingredients which can be employed in the compositions used in the method of the present invention are thickeners and binders. A thickener or binder will usually be present in amounts anywhere from 0.01% to 20% by weight, preferably from about 0.1% to about 10%, more preferably from about 0.1% to about 5% by weight of the composition. Suitable thickeners include cross-linked polyacrylate materials available under the trademark Carbopol from the B. F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality.

Preferred binders include, but are not limited to methycellulose, sodium carboxymethycellulose, hydroxypropylmethylcellulose, carbomer, polyvinylpyrrolidone, acacia, guar gum, xanthan gum and tragacanth. Particularly preferred are methycellulose, carbomer, xanthan gum, guar gum, polyvinylpyrrolidone and sodium carboxymethycellulose 5. Flavoring Agents Flavoring agents among those useful herein include those described in Remington's *Pharmaceutical Sciences*, 18th Edition, Mack Publishing Company, 1990, pp. 1288–1300, incorporated by reference herein. Dyes, or pigments among those useful herein include those described in *Handbook of Pharmaceutical Excipients*, Second Edition pp. 126–134, 1994 by the American Pharmaceutical Association & the Pharmaceutical Press, incorporated by reference herein.

6. Buffering Systems

Preferred buffer systems include, but are not limited to potassium acetate, boric carbonic, phosphoric, succinic, malic, tartaric, citric, acetic, benzoic, lactic, glyceric, gluconic, glutaric and glutamic. Particularly preferred are phosphoric, tartaric, citric, and potassium acetate.

7. Preservatives

Preferred preservatives include, but are not limited to, phenol, alkyl esters of parahydroxybenzoic acid, benzoic acid and the salts thereof, boric acid and the thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, benzalkonium chloride, methyl paraben and propyl paraben.

8. Sweeteners

Preferred sweeteners include, but are not limited to, sucrose, glucose, saccharin, and aspartame. Particularly preferred are sucrose and saccharin.

9. Fillers

Preferred fillers include, but are not limited to lactose, sucrose, maltodextrin, mannitol, starch 1500, dicalcium phosphate and microcrystalline cellulose.

10. Plasticizers

Preferred plasticizers include, but are not limited to polyethylene glycol, propylene glycol, dibutyl phthalate, and castor oil, acetylated monoglycerides, and triacetin.

11. Lubricants

Preferred lubricants include, but are not limited to, magnesium stearate, stearic acid, and talc.

12. Disintegrants

Preferred disintegrants include, but are not limited to, crospovidone, sodium carboxymethyl starch, sodium starch glycolate, sodium carboxymethyl cellulose, alginic acid, clays, and ion exchange resins.

13. Polymers

Preferred polymers, include but are not limited to hydroxypropylmethylcellulose (HPMC) alone and/or in combination with hydroxypropylcellulose (HPC), carboxymethylcellulose, acrylic resins such as Eudragit® RL30D, manufactured by Rohm Pharma GmbH Weiderstadt, West Germany, methylcellulose, ethylcellulose, and polyvinylpyrrolidone or other commercially available film-coating preparations such as Dri-Klear, manufactured by Crompton & Knowles Corp., Mahwah, N.J. or Opadry manufactured by Colorcon, West Point, Pa.

C. Other Ingredients

In addition to the vehicle and the triterpene acids hereinbefore described, the compositions of the present invention may also contain other ingredients as set forth hereinafter.

1. Other Hair Growth Agents

The compositions herein can include other hair growth agents including, but not limited to, zinc salts of carboxylic acids, saponins such as those described in EP 0,558,509 to Bonte et al, published Sep. 8, 1993 and WO 97/01346 to Bonte et al, published Jan. 16, 1997 (both of which are herein incorporated by reference), other triterpenes such as oleanolic acid and ursolic acid, crataegolic acid, celastrol, asiatic acid, inhibitors of 5-α-reductase such as progesterone, 1,4-methyl-4-azasteroids, in particular 17-β-N,N-diethylcarbamoyl-4-methyl-4-aza-5-α-androstan-3-one, androgen receptor antagonists such as cyproterone acetate, Minoxidil®, azelaic acid and its derivatives, cyclosporin, triiodothyronine, diazoxide, potassium channel openers such as cromakalin, phenytoin and mixtures thereof.

Other hair growth agents are described in detail in, for example, JP 09-157,139 to Tsuji et al, published Jun. 17, 1997; EP 0277455 A1 to Mirabeau, published Aug. 10, 1988; WO 97/05887 to Cabo Soler et al, published Feb. 20, 1997; WO 92/16186 to Bonte et al, published Mar. 13, 1992; JP 62-93215 to Okazaki et al, published Apr. 28, 1987; U.S. Pat. No. 4,987,150 to Kurono et al, issued Jan. 22, 1991; JP 290811 to Ohba et al, published Oct. 15, 1992; JP 05-286, 835 to Tanaka et al, published Nov. 2, 1993, FR 2,723,313 to Greff, published Aug. 2, 1994, U.S. Pat. No. 5,015,470 to Gibson, issued May 14, 1991, all of which are herein incorporated by reference.

These hair growth agents are typically employed in the compositions herein at a level ranging from about 0.01% to about 15%, preferably from about 0.1% to about 10%, most preferably from about 0.5% to about 5% by weight of the composiiton.

2. Other Hair Growth Agents

The compositions herein may also optionally comprise an activity enhancer or enhancers. The activity enhancer or enhancers can be chosen from a wide variety of molecules which can function in different ways to enhance the hair growth effects of a compound of the present invention. These optional activity enhancers, when present, are typically employed in the compositions herein at a level ranging from about 0.01% to about 15%, preferably from about 0.1% to about 10%, most preferably from about 0.5% to about 5% by weight of the composition.

Vasodilators such as potassium channel agonists including, for example, minoxidil and minoxidil derivatives such as aminexil and such as those described in U.S. Pat. No. 3,382,247, U.S. Pat. No. 5,756,092, issued May 26, 1998, U.S. Pat. No. 5,772,990, issued Jun. 30, 1998, U.S. Pat. No. 5,760,043, issued Jun. 2, 1998, U.S. Pat. No. 328,914, issued Jul. 12, 1994, U.S. Pat. No. 5,466,694, issued Nov. 14, 1995, U.S. Pat. No. 5,438,058, issued Aug. 1, 1995, and U.S. Pat. No. 4,973,474, issued Nov. 27, 1990, (all of which are herein incorporated by reference), and cromakalin and diazoxide can be used as optional activity enhancers in the compositions herein.

One suitable class of optional activity enhancer for use herein are antiandrogens. Examples of suitable antiandrogens may include, but are not limited 5-α-reductase inhibitors such as finesteride and those described in U.S. Pat. No. 5,516,779, issued May 14, 1996 (herein incorporated by reference) and in Nnane et al, *Cancer Research* 58, "Effects of Some Novel Inhibitors of C17,20-Lyase and 5α-Reductase in Vitro and in Vivo and Their Potential Role in the Treatment of Prostate Cancer., as well as cyproterone acetate, azelaic acid and its derivatives and those compounds described in U.S. Pat. No. 5,480,913, issued Jan. 2, 1996, flutamide, and those described in U.S. Pat. No. 5,411,981, issued May 2, 1995, U.S. Pat. No. 5,565,467, issued Oct. 15, 1996 and U.S. Pat. No. 4,910,226, issued Mar. 20, 1990, all of which are herein incorporated by reference.

Another suitable class of optional activity enhancers are immunosuppressants such as 1) cyclosporin and cyclosporin analogs including those described in U.S. Provisional Patent Application No. 60/122,925, Fulmer et al., "Method of Treating Hair Loss Using Non-Immunosuppressive Compounds", filed Mar. 5, 1999, herein incorporated by reference, and 2) FK506 analogs such as those described in U.S. Provisional Patent Application No. 60/102,449, McIver et al., "Heterocyclic 2-Substituted Ketoamides", filed Sep. 30, 1998, U.S. Provisional Patent Application No. 60/102,448, McIver et al., "2-Substituted Ketoamides", filed Sep. 30, 1998, U.S. Provisional Patent Application No. 60/102,539, McIver et al., "2-Substituted Heterocyclic Sulfonamides", filed Sep. 30, 1998, U.S. Provisional Patent Application No. 60/102,458, Tiesman et al., "Method of Treating Hair Loss Using Ketoamides", filed Sep. 30, 1998, and U.S. Provisional Patent Application No. 60/102,437, McIver et al., "Method of Treating Hair Loss Using Sulfonamides", filed Sep. 30, 1998, all of which are herein incorporated by reference.

Another suitable class of optional activity enhancers are antimicrobials such as selenium sulfide, ketoconazole, triclocarbon, triclosan, zinc pyrithione, itraconazole, asiatic acid, hinokitiol, mipirocin and those described in EPA 0,680,745 (herein incorporated by reference), clinacycin hydrochloride, benzoyl peroxide, benzyl peroxide and minocyclin.

Anti-inflammatories can also be incorporated into the compositions herein as an optional activity enhancer. Examples of suitable anti-inflammatories may include glucocorticoids such as hydrocortisone, mometasone furoate and prednisolone, nonsteroidal anti-inflammatories including cyclooxygenase or lipoxygenase inhibitors such as those described in U.S. Pat. No. 5,756,092, and benzydamine, salicylic acid, and those compounds described in EPA 0,770, 399, published May 2, 1997, WO 94/06434, published Mar. 31, 1994 and FR 2,268,523, published Nov. 21, 1975, all of which are herein incorporated by reference.

Another suitable class of optional activity enhancers are thyroid hormones and derivatives and analogs thereof. Examples of suitable thyroid hormones for use herein may include triiodothyrionine. Examples of thyroid hormone analogs which may be suitable for use herein include those described in U.S. Provisional Patent Application No. 60/136,996, Zhang et al., "Method of Treating Hair Loss", filed Jun. 1, 1999, U.S. Provisional Patent Application No. 60/137,024, Zhang et al., "Method of Treating Hair Loss Using Biphenyl Compounds", filed Jun. 1, 1999, U.S. Provisional Patent Application No. 60/137,022, Zhang et al., "Method of Treating Hair Loss Using Carboxyl Derivatives", filed Jun. 1, 1999, U.S. Provisional Patent Application No. 60/137,023, Zhang et al., "Method of Treating Hair Loss Using Sulfonyl Thyromimetic Compounds", filed Jun. 1, 1999, U.S. Provisional Patent Application No. 60/137,052, Youngquist et al., "Biaryl Compounds", filed Jun. 1, 1999, U.S. Provisional Patent Application No. 60/137,063, Youngquist et al., "Sulfur-Bridged Compounds", filed Jun. 1, 1999, and U.S. Provisional Patent Application No. 60/136,958, Youngquist et al., "Substituted Biaryl Ether Compounds", filed Jun. 1, 1999.

Prostaglandin agonists or antagonists can also be used as optional activity enhancers in the compositions herein. Examples of suitable prostaglandins agonists or antagonists include latanoprost and those described in WO 98/33497, Johnstone, published Aug. 6, 1998, WO 95/11003, Stjernschantz, published Apr. 27, 1995, JP 97-100091, and Ueno, JP 96-134242, Nakamura.

Another class of optional activity enhancers for use herein are retinoids. Suitable retinoids may include isotretinoin, acitretin, tazarotene.

Non-limiting examples of penetration enhancers which may be used as optional activity enhancers herein include, for example, 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan- 1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic acid, methylsulfoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one and those described in U.S. Pat. No. 5,015,470, issued May 14, 1991 and U.S. Pat. No. 5,496,827, issued Jul. 15, 1994 (both of which are herein incorporated in its entirety by reference).

Other classes of optional activity enhancers for use herein include flavinoids, ascomycin derivatives and analogs, histamine antagonists such as diphenhydramine hydrochloride, other triterpenes such as oleanolic acid and ursolic acid and those described in U.S. Pat. No. 5,529,769, JP 10017431, WO 95/35103, U.S. Pat. No. 5,468,888, JP 09067253, WO 92/09262, JP 62093215, U.S. Pat. No. 5,631,282, U.S. Pat. No. 5,679,705, JP 08193094, saponins such as those described in EP 0,558,509 to Bonte et al, published Sep. 8, 1993 and WO 97/01346 to Bonte et al, published Jan. 16, 1997 (both of which are herein incorporated by reference in their entirety), proeoglycanase or glycosaminoglycanase inhibitors such as those described in U.S. Pat. No. 5,015,470, issued May 14, 1991, U.S. Pat. No. 5,300,284, issued Apr. 5, 1994 and U.S. Pat. No. 5,185,325, issued Feb. 9, 1993 (all of which are herein incorporated in their entirety by reference) estrogen agonists and antagonists, pseudoterins, cytokine and growth factor promoters, analogs or inhibitors such as interleukin1 inhibitors, interleukin-6 inhibitors, interleukin-10 promoters, and tumor necrosis factor inhibitors, vitamins such as vitamin D analogs and parathyroid hormone antagonists, Vitamin B12 analogs and panthenol, interfuron agonists and antagonists, hydroxyacids such as those described in U.S. Pat. No. 5,550,158, benzophenones and hydantoin anticonvulsants such as phenytoin.

Other hair growth agents are described in detail in, for example, JP 09-157,139 to Tsuji et al, published Jun. 17, 1997; EP 0277455 A1 to Mirabeau, published Aug. 10, 1988; WO 97/05887 to Cabo Soler et al, published Feb. 20, 1997; WO 92/16186 to Bonte et al, published Mar. 13, 1992; JP 62-93215 to Okazaki et al, published Apr. 28, 1987; U.S. Pat. No. 4,987,150 to Kurono et al, issued Jan. 22, 1991; JP 290811 to Ohba et al, published Oct. 15, 1992; JP 05-286, 835 to Tanaka et al, published Nov. 2, 1993, FR 2,723,313 to Greff, published Aug. 2, 1994, U. S. Pat. No. 5,015,470 to Gibson, issued May 14, 1991, U.S. Pat. No. 5,559,092, issued Sep. 24, 1996, U.S. Pat. No. 5,536,751, issued Jul. 16, 1996, U.S. Pat. No. 5,714,515, issued Feb. 3, 1998, EPA 0,319,991, published Jun. 14, 1989, EPA 0,357,630, published Oct. 6, 1988, EPA 0,573,253, published Dec. 8, 1993, JP 61-260010, published Nov. 18, 1986, U.S. Pat. No. 5,772,990, issued Jun. 30, 1998, U.S. Pat. No. 5,053, 410, issued Oct. 1, 1991, and U.S. Pat. No. 4,761,401, issued Aug. 2, 1988, all of which are herein incorporated by reference.

3. Miscellaneous

The compositions of the present invention can comprise a wide range of other optional components. These additional components should be pharmaceutically acceptable. The *CTFA Cosmetic Ingredient Handbook*, Second Edition, 1992, which is incorporated by reference herein in its entirety, describes a wide variety of non-limiting cosmetic and pharmaceutical ingredients commonly used in the skin care industry, which are suitable for use in the compositions of the present invention. Non-limiting examples of functional classes of ingredients are described at page 537 of this reference. Examples of these and other functional classes include: abrasives, absorbents, anticaking agents, antioxidants, vitamins, biological additives, bulking agents, chelating agents, chemical additives, colorants, cosmetic astringents, cosmetic biocides, denaturants, drug astringents, external analgesics, film formers, fragrance components, opacifying agents, pH adjusters, propellants, reducing agents, and skin bleaching agents.

II. METHOD OF MANUFACTURE

The compositions of the present invention are prepared according to conventional methods known in the art.

III. METHOD OF USE

The compositions of the present invention are especially useful for regulating hair growth in mammals (e.g., humans and domestic animals). In one embodiment, the present invention provides for the prevention of hair loss. In another embodiment, the present invention provides for the use of the compositions described herein for stimulating new hair growth.

The compositions of the present invention can be administered topically, orally or parenterally. The preferred method of the present invention involves the topical application of the compositions described herein to the scalp, particularly where the scalp is already bald or balding. The amount of the composition and the frequency of application to the hair and/or scalp/skin can vary widely, depending on the desired effect and/or personal needs. Typically the composition is applied from about 1 to about 10 times per day, more typically from about 1 to about 6 times per day and most typically from 1 to 3 times per day.

The topical compositions can be delivered the hair/scalp/skin from a variety of delivery devices. For example, the compositions can be incorporated into a medicated cleansing pad. Preferably these pads comprise form about 50% to about 75% of a substrate and from about 25% to about 50% of a liquid composition deliverable from the substrate. Suitable pads are described, for example, in U.S. Pat. No. 4,891,228; Thurman et al.; issued Jan. 2, 1990; and U.S. Pat. No. 4,891,227; Thaman et al.; issued Jan. 2, 1990, both of which are incorporated by reference.

Alternatively, the compositions useful herein can be incorporated into and delivered from a soft-tipped or flexible dispensing device. These devices are useful for the controlled delivery of the compositions to the skin surface and have the advantage that the treatment composition itself never need be directly handled by the user. Non-limiting examples of these devices comprise a fluid container including a mouth, an applicator, means for holding the applicator in the mouth of the container and a normally closed pressure-responsive valve for permitting the flow of fluid from the container to the applicator upon the application of pressure to the valve. The fluid preferably contains from about 0.01% to about 20% of triterpene acid, preferably from about 0.1% to about 10%, more preferably from about 1% to about 5%,.

The valve can include a diaphragm formed from an elastically fluid impermeable material with a plurality of non-intersecting acruate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623 to Schwartzman; issued Sep. 25, 1987; U.S. Pat. No. 3,669,323; Harker et al.; issued Jun. 13, 1972; U.S. Pat. No. 3,418,055; Schwartzman; issued Dec. 24, 1968; and U.S. Pat. No. 3,410,645; Schwartzman; issued Nov. 12, 1968; all of which are herein incorporated by reference. Examples of applicators useful herein are commercially available from Dab-O-Matic, Mount Vernon, N.Y.

Topical compositions of the present invention can also be delivered via conventional hair care products, including, but not limited to shampoos, conditioners, styling products or other leave-in or rinse off products.

EXAMPLES

Example 1–5 are non-limiting examples of topical compositions of the present invention:

| Ingredient | Example 1 (% by weight) | Example 2 (% by weight) | Example 3 (% by weight) | Example 4 (% by weight) | Example 5 (% by weight) |
|---|---|---|---|---|---|
| Betulinic acid | 5.0 | 0.0 | 3.0 | 3.0 | 3.0 |
| Betulonic Acid | 0.0 | 3.0 | 0.0 | 0.0 | 0.0 |
| Minoxidil | 0.0 | 0.0 | 0.0 | 0.0 | 2.0 |
| Tween 20 | 1.0 | 0.0 | 0.20 | 0.0 | 0.0 |
| isopropyl alcohol | 47.0 | 48.5 | 48.5 | 48.5 | 47.5 |
| propylene glycol | 28.2 | 29.1 | 29.1 | 29.1 | 28.5 |
| dimethyl-isosorbide | 18.8 | 19.4 | 0.0 | 18.9 | 18.1 |
| $C_{12}14\ C_{15}$ alkyl octanoate | 0.0 | 0.0 | 19.1 | 0.0 | 0.0 |
| hydroxy-propyl cellulose | 0.0 | 0.0 | 0.10 | 0.0 | 0.0 |
| poly-quatemium 10 | 0.0 | 0.0 | 0.0 | 0.50 | 1.0 |
| Total | 100.0 | 100.0 | 100.0 | 100.0 | 100.0 |

Example 1 is prepared as follows:
1. Add the isopropyl alcohol and Tween 20 into mixing container and agitate until combined.
2. Add betulinic acid into the isopropyl alcohol and Tween solution and mix with a high shear mixer for 10 minutes.
3. Add the remaining ingredients and mix an additional 10 minutes.

Example 2 is prepared as follows:
1. Combine the isopropyl alcohol, propylene glycol and dimethylisosobide into mixing container and mix until in a clear solution.
2. Add the betulonic acid to the combined solution and mix until in a clear solution.

Example 3 is prepared as follows:
1. Add the isopropyl alcohol and Tween 20 into mixing container and agitate until combined.
2. Add betulinic acid into the isopropyl alcohol and Tween solution and mix with a high shear mixer for 10 minutes.
3. Add the propylene glycol and C12–C15 alkyl octanoate to the mixture and mix an additional 10 minutes.
4. Add in the hydroxypropyl cellulose to the mixture and mix with a standard mixer for 4 to 5 hours.

Examples 4 and 5 are prepared as follows:
1. Add the isopropyl alcohol and polyquaternium 10 into mixing container and mix for 1 to 2 hours.
2. Add betulinic acid into the isopropyl alcohol and polyquaternium 10 mixture and mix with a high shear mixer for 10 minutes.
3. Add the remaining ingredients and mix an additional 10 minutes.

Examples 6 and 7 are non-limiting examples of tablet compositions of the present invention:

| Ingredient | Example 6 (mg) | Example 7 (mg) |
|---|---|---|
| Betulinic acid | 100 | 0.25 |
| Crospovidone | 15 | 0.0 |
| Lactose, hydrous | 200 | 0.0 |
| Microcrystalline cellulose | 80 | 0.0 |
| Magnesium stearate | 5 | 2.0 |
| Polyvinylpyrrolidone | 0.0 | 3.0 |
| Sodium starch glycolate | 0.0 | 2.0 |

-continued

| Ingredient | Example 6 (mg) | Example 7 (mg) |
|---|---|---|
| Dicalcium phosphate | 0.0 | 75.0 |
| Talc | 0.0 | 2.75 |
| Methanol | 0.0 | 20.0 |
| Starch 1500 | 0.0 | 15.0 |

Example 6 is prepared as follows:
1. Add the betulinic acid, the crospovidone and the microcrystalline cellulose into a twin-shell blender and mix for 20 minutes.
2. Sieve the mixture through a 40 mesh screen and return to the twin-shell blender.
3. Add the lactose hydrous and mix for 25 minutes.
4. Add the magnesium stearate and mix for 5 minutes.
5. Compress into tablets on a standard rotary tablet press.

Example 7 is prepared as follows:
1. Dissolve the betulinic acid and polyvinylpyrrolidone in the methanol under agitation.
2. Add the sodium starch glycolate, dicalcium phosphate, and starch 1500 into a high shear mixer and mix for 15 minutes.
3. Add the methanol solution to the high-shear blender over a 10 minute period and then mix for an additional 10 minutes until granules are formed.
4. Transfer the wetted mass into a fluid bed dryer and dry at 45° C. for 2 hours.
5. Sieve the dried granules through a 30 mesh screen and transfer back to the high-shear blender.
6. Add the talc and magnesium stearate and mix for 3 minutes.
7. Compress into tablets on a standard rotary tablet press Example 8 is a non-limiting example of a composition according to the present invention. This composition can be injected subcutaneously.

| Ingredient | Example 8 (mg/mL) |
|---|---|
| Betulinic acid | 1.0 |
| Dibasic sodium phosphate | 7.0 |

-continued

| Ingredient | Example 8 (mg/mL) |
|---|---|
| Monobasic sodium phosphate | 3.0 |
| Edetate disodium | 0.1 |
| Benzalkonium chloride | 0.1 |
| Water for injection | QS to 10 liters |

Example 8 is prepared as follows:
1. The betulinic acid is micronized in a jet mill and sterilized by exposing it to 2.5 Mrad of radiation from a cobalt 60 source.
2. The dibasic sodium phosphate, monobasic sodium phosphate, edetate disodium, and benzalkonium chloride are dissolved in 9 liters of water for injection in a standard mixing tank.
3. The solution is filtered through a 0.22 micron filter to achieve sterilization.
4. The betulinic acid is added and mixed for 30 minutes under agitation.
5. The suspension is aseptically filled into 3 mL flint glass vials, stoppered and sealed on standard filling equipment.

What is claimed is:

1. A composition which comprises a pharmaceutically or cosmetically acceptable vehicle and from 0.00001% to about 99.9% of betulonic acid and minoxidil.

2. A composition which comprises:
   a) a pharmaceutically or cosmetically acceptable vehicle;
   b) from about 0.0001% to about 99.9% of betulonic acid, or one or more salts thereof; and
   c) a hair growth agent selected from the group consisting of vasodilators, antiandrogens, immunosuppressants, antiinflammatories, antimicrobials, thyroid hormones, prostoglandins, retinoids, vitamin D analogs, and parathyroid hormone analogs.

3. The composition of claim 2 which is a topical composition.

4. The composition of claim 3 wherein the pharmaceutically or cosmetically acceptable vehicle is present at a level ranging from about 50% to about 99.99% by weight of the composition.

* * * * *

UNITED STATES PATENT AND TRADEMARK OFFICE
CERTIFICATE OF CORRECTION

PATENT NO.    : 6,482,857 B1
DATED         : November 19, 2002
INVENTOR(S)   : Barton James Bradbury et al.

It is certified that error appears in the above-identified patent and that said Letters Patent is hereby corrected as shown below:

<u>Column 1,</u>
Line 10, "Jul. 1, 1998" should be -- July 17, 1998 --.

Signed and Sealed this

Twenty-sixth Day of August, 2003

JAMES E. ROGAN
*Director of the United States Patent and Trademark Office*